(12) United States Patent
Cho et al.

(10) Patent No.: US 8,838,197 B2
(45) Date of Patent: Sep. 16, 2014

(54) MICRO PROBE AND MANUFACTURING METHOD THEREOF

(71) Applicant: Korea Institute of Science and Technology, Seoul (KR)

(72) Inventors: Il Joo Cho, Seoul (KR); Eui Sung Yoon, Seoul (KR); Jei Won Cho, Uiwang (KR); Myoung Gun Jeon, Bucheon (KR); Yun Kyung Kim, Seoul (KR)

(73) Assignee: Korea Institute of Science and Technology, Seoul (KR)

( * ) Notice: Subject to any disclaimer, the term of this patent is extended or adjusted under 35 U.S.C. 154(b) by 44 days.

(21) Appl. No.: 13/670,957

(22) Filed: Nov. 7, 2012

(65) Prior Publication Data
US 2013/0123599 A1    May 16, 2013

(30) Foreign Application Priority Data
Nov. 11, 2011 (KR) .................. 10-2011-0117435

(51) Int. Cl.
*A61B 5/0478* (2006.01)
*A61B 5/00* (2006.01)

(52) U.S. Cl.
CPC ........... *A61B 5/0478* (2013.01); *A61B 2503/42* (2013.01); *A61B 5/6868* (2013.01); *A61B 2562/18* (2013.01); *A61B 2562/125* (2013.01); *A61B 2503/40* (2013.01)
USPC ......................................... 600/378; 607/116

(58) Field of Classification Search
CPC .. A61B 5/04001; A61B 5/0478; A61B 5/685; A61B 5/6868; A61N 1/0526; A61N 1/0529; A61N 1/0531; A61N 1/0534
USPC ............................ 600/373, 377, 378; 607/116
See application file for complete search history.

(56) References Cited

U.S. PATENT DOCUMENTS

| | | | |
|---|---|---|---|
| 8,306,632 B2* | 11/2012 | Schouenborg | 607/117 |
| 8,442,614 B2* | 5/2013 | Schulman | 600/378 |
| 2008/0255439 A1 | 10/2008 | Tang et al. | |
| 2009/0177144 A1 | 7/2009 | Masmanidis et al. | |
| 2010/0308456 A1 | 12/2010 | Wise et al. | |
| 2011/0125001 A1 | 5/2011 | Fang et al. | |
| 2011/0144467 A1 | 6/2011 | Yao et al. | |
| 2011/0144471 A1 | 6/2011 | Hsu et al. | |
| 2012/0123318 A1* | 5/2012 | Ek et al. | 604/20 |
| 2013/0150931 A1* | 6/2013 | Kipke et al. | 607/116 |

OTHER PUBLICATIONS

Fan Wu et al., "A Flexible Fish-Bone-Shaped Neural Probe Strengthened by Biodegradable Silk Coating for Enhanced Biocompatibility", Transducers '11, Beijing, China, Jun. 5-9, 2011, pp. 966-969.
Arash A. Fomani et al., "Fabrication and characterization of the flexible neural microprobes with improved structural design", Sensors and Actuators A 168, 2011, pp. 233-241.

* cited by examiner

*Primary Examiner* — Lee S Cohen
(74) *Attorney, Agent, or Firm* — Staas & Halsey LLP (57) ABSTRACT

The micro probe according to an embodiment of the present disclosure includes: a probe portion made of a rigid material and serving as a portion inserted into the brain; a flexible portion connected to a distal end of the probe portion and made of a flexible material; a soluble portion coated on at least one surface of the flexible portion and made of a material which is dissolved by a solution in the cranium; and a body portion connected to the other end of the flexible portion whose one end is connected to the probe portion.

4 Claims, 8 Drawing Sheets

MICRO PROBE AND MANUFACTURING METHOD THEREOF

CROSS-REFERENCE TO RELATED APPLICATION

This application claims priority to Korean Patent Application No. 10-2011-0117435, filed on Nov. 11, 2011, and all the benefits accruing therefrom under 35 U.S.C. §119, the contents of which in its entirety are herein incorporated by reference.

BACKGROUND

1. Field

The present disclosure relates to a micro probe and a manufacturing method thereof, and more particularly, to a micro probe and a manufacturing method thereof, which allows the micro probe to be inserted into the brain while maintaining the insertion intensity of the micro probe, and after the probe being inserted into the brain, allows the soluble portion keeping the insertion intensity to be dissolved in the solution in the cranium to expose flexible material, thereby minimizing the damage of neurons of the brain even though the probe is used for a long time.

2. Description of the Related Art

Recent studies are actively made to treat the cerabropathy and investigate operations of the brain by detecting and analyzing cranial nerve stimuli and resultant signals. In particular, in order to measure many brain signals at several portions simultaneously and minimize the damage of neurons, an MEMS cranial neural probe with a small size where several electrodes are integrated has been developed. However, since conventional MEMS probes are mostly made of rigid silicon entirely, the probes consistently apply stimuli to the brain after being inserted into the brain causing continued damage. Since the body where the probe is connected is fixed to the outside of the brain and the probe is inserted into the flexible brain, when the brain breathes or an experimental subject where the probe is inserted into the brain moves, the brain also moves and accordingly the probe consistently stimulates the flexible brain.

However, since conventional MEMS probes are mostly made of rigid silicon entirely, the probes consistently apply stimuli to the brain after being inserted into the brain to remain damages. Since the body where the probe is connected is fixed to the outside of the brain and the probe is inserted into the flexible brain, when the brain breathes or an experimental subject where the probe is inserted into the brain moves, the brain also moves and accordingly the probe consistently stimulates the flexible brain.

In order to solve the above problem, it has been attempted to make the probe with flexible material. However, if the probe is made of flexible material, the probe should have a great thickness or be reinforced with a structure for insertion in order to maintain the intensity when the probe is inserted, and so the brain damage at the insertion of the probe increases.

In this regard, US Unexamined Patent Publication No. 2011/0144471 discloses a probe made of flexible material, where the probe should be inserted by making the probe with a great thickness or using an inserting device when the probe is inserted for the in-vivo test. Therefore, when the probe is inserted, the brain damage increases.

The thesis "Fabrication and characterization of the flexible neural microprobes with improved structural design" is directed to decreasing the damage at the insertion into the brain by making a probe with flexible material. However, the micro probe of the above paper has a metallic layer interposed between flexible polyimide layers in order to maintain the insertion intensity, and so the entire thickness of the probe increases, and its manufacturing process is complicated.

In addition, the thesis "A flexible fish-bone-shaped neural probe strengthened by biodegradable silk coating for enhanced biocompatibility" discloses that the entire probe is coated with silk which can be dissolved in the brain, in order to maintain the insertion intensity of the probe made of flexible material. However, in this case, the entire thickness of the probe increases, which generates great brain damage at insertion, and in case where the silk inserted into the brain is not completely dissolved, the silk may cover the electrode and disturb recording of neural signals.

RELATED LITERATURES

Patent Literature

US Unexamined Patent Publication No. 2011/0144471

Non-Patent Literature

Non-patent Literature 1: Fabrication and characterization of the flexible neural microprobes with improved structural design: Arash A. Fomani et al., Sensors and Actuators A 168, 2011, pp. 233-241

Non-patent Literature 2: A flexible fish-bone-shaped neural probe strengthened by biodegradable silk coating for enhanced biocompatibility: Fan Wu et al., Transducers' 11, Beijing, China, Jun. 5-9, 2011, pp. 966-969

SUMMARY

The present disclosure is directed to providing a micro probe and manufacturing method thereof, which may minimize the brain damage after the probe is inserted, while maintaining the insertion intensity of the inserted probe.

In one aspect, there is provided a micro probe, which includes: a probe portion made of a rigid material and serving as a portion inserted into the brain; a flexible portion connected to a distal end of the probe portion and made of a flexible material; a soluble portion coated on at least one surface of the flexible portion and made of a material which is dissolved by a solution in the cranium; and a body portion connected to the other end of the flexible portion whose one end is connected to the probe portion, wherein, after the probe portion maintaining the insertion intensity by the soluble portion is inserted into the brain through an opening formed in a part of the cranium, the soluble portion is dissolved by the solution in the cranium to expose the flexible portion, and the body portion is disposed and used at the outside of the cranium.

An electrode may be disposed at a proximal end of the probe portion, and a signal line connected to the electrode may extend to the body portion through the probe portion and the flexible portion.

The flexible portion may be made of polyimide, parylene, polydimethylsiloxane or benzocyclobutene.

The soluble portion may be made of sucrose or silk.

The flexible portion may be formed with a lattice pattern.

In another aspect, there is provided a manufacturing method of a micro probe, which includes: forming an electrode pattern and a signal line on a wafer; etching a partial region of the wafer where the signal line passes, by means of an etching process; depositing a flexible portion at the etched partial region of the wafer; removing a region including a lower region of the flexible portion from the wafer by means of a releasing process; and coating at least one surface of the flexible portion with a soluble portion.

Before the etching of a partial region of the wafer by means of an etching process, the manufacturing method of a micro probe may further include depositing a passivation layer on the signal line.

The manufacturing method of a micro probe may further include etching the passivation layer deposited on the electrode by means of an etching process to expose the electrode.

The partial region of the wafer may be etched into a lattice pattern by means of the etching process.

The flexible portion may be made of polyimide, parylene, polydimethylsiloxane or benzocyclobutene.

The soluble portion may be made of sucrose or silk.

The micro probe and the manufacturing method thereof according to the present disclosure give the effect of maintaining the insertion intensity of the probe when the probe is inserted into the brain, due to the soluble portion coated on the flexible portion of the probe.

In addition, the micro probe and the manufacturing method thereof according to the present disclosure give the effect of minimizing the brain damage caused by the probe, since, after the probe portion of the probe is inserted into the brain, the soluble portion is dissolved by the solution in the cranium to expose the expose the flexible portion, thereby lessening the vibration caused by the flexible portion even though the experimental subject moves.

BRIEF DESCRIPTION OF THE DRAWINGS

The above and other aspects, features and advantages of the disclosed exemplary embodiments will be more apparent from the following detailed description taken in conjunction with the accompanying drawings in which.

DETAILED DESCRIPTION OF MAIN ELEMENTS

100: micro probe
110: probe portion
112: electrode
114: signal line
120: flexible portion
130: soluble portion
140: body portion
510: wafer
510a: lower silicon
510b: insulation substrate
510c: upper silicon
520: electrode
530: signal line
540: passivation layer
550: flexible portion
560: soluble portion

DETAILED DESCRIPTION

Hereinafter, a micro probe and a manufacturing method thereof according to exemplary embodiments of the present disclosure will be described in detail with reference to the accompanying drawings.

Figure 1:
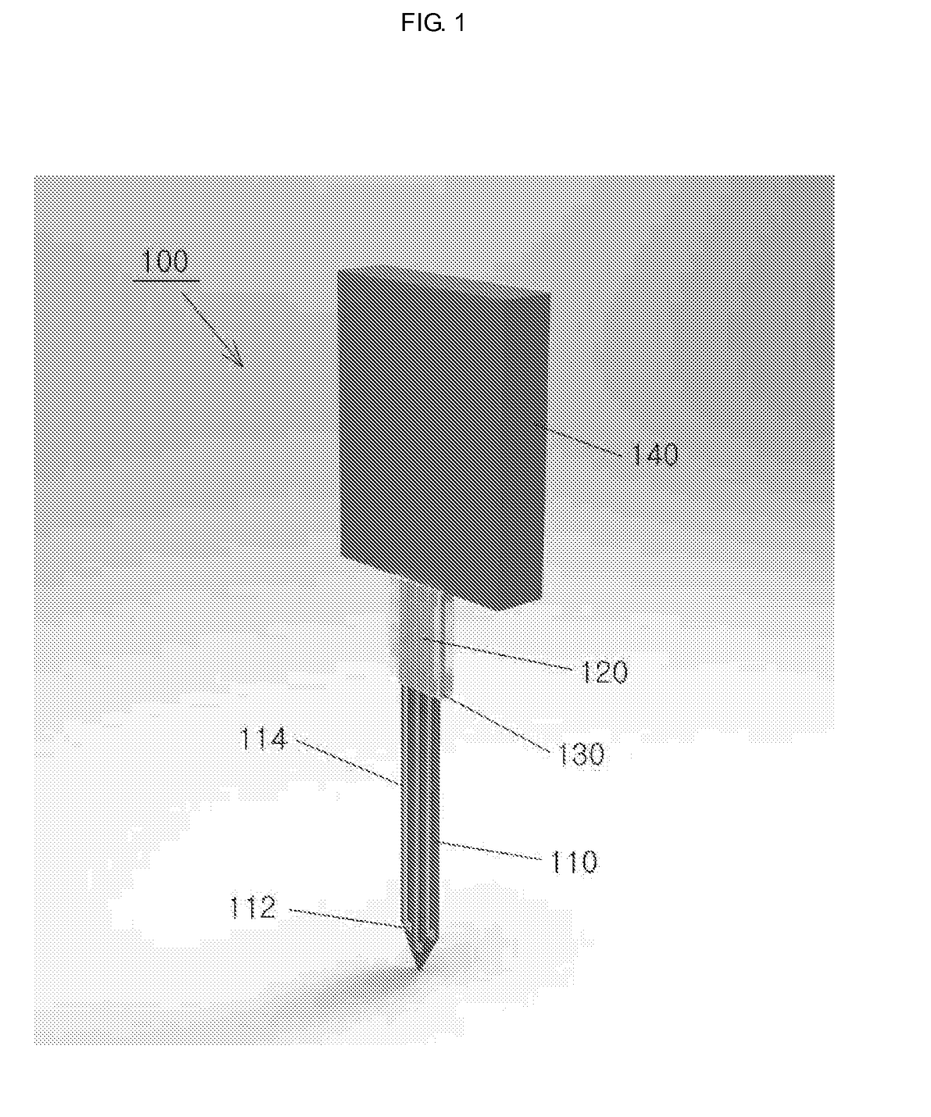
FIG. 1 is a perspective view showing a micro probe according to an embodiment of the present disclosure.
Figure 2:
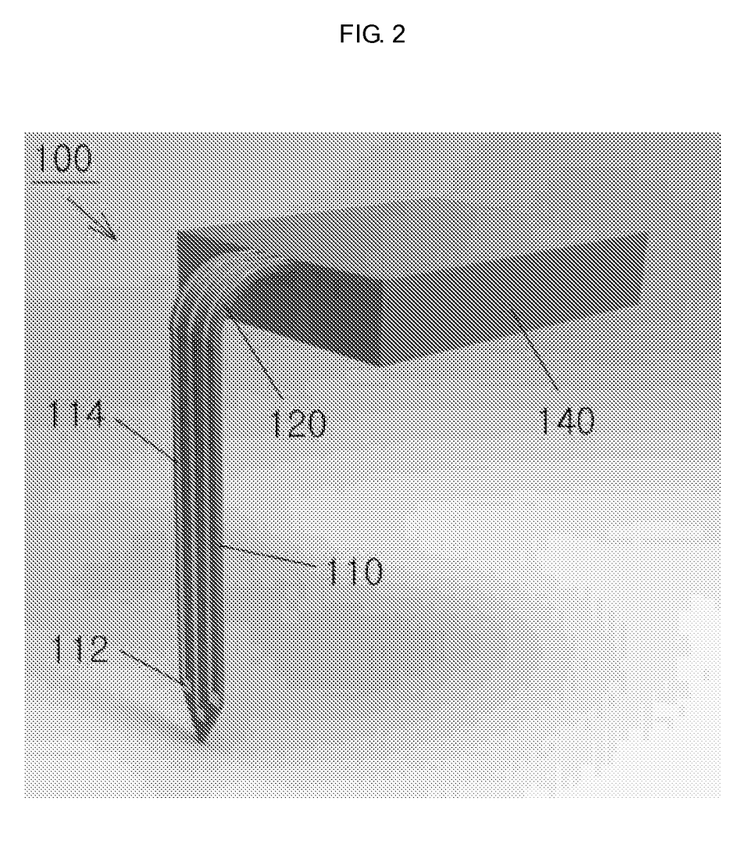
FIG. 2 is a perspective view showing a flexible portion exposed since a soluble portion of the micro probe of FIG. 1 is dissolved.

FIG. 1 is a perspective view showing a micro probe according to an embodiment of the present disclosure, and FIG. 2 is a perspective view showing a flexible portion exposed since a soluble portion of the micro probe of FIG. 1 is dissolved.

Referring to FIG. 1, a micro probe 100 of the present disclosure includes a probe portion 110, a flexible portion 120, a soluble portion 130 and a body portion 140.

The probe portion 110 is made of a rigid material and serves as a portion inserted into the brain. The probe portion 110 may be made of, for example, silicon with suitable strength and biocompatibility, and the probe portion 110 may be inserted into the relatively soft brain without the addition of an auxiliary device for reinforcing the insertion intensity while maintaining a small thickness due to its rigidity. Therefore, when the probe portion 110 is inserted, the invaded region of the brain may be minimized, which lowers the possibility of a brain damage. An electrode 112 is disposed at a proximal end of the probe portion 110, and a signal line 114 connected to the electrode 112 extends through the probe portion 110 and the flexible portion 120 to a body portion 140.

The flexible portion 120 is connected to a distal end of the probe portion 110 and is made of a flexible material. The flexible portion 120 connects the probe portion 110 and the body portion 140, and lessens vibrations even though the body portion 140 moves, thereby relieving the shaking of the probe portion 110. Therefore, even though an experimental subject where a probe is inserted, for example an experimental rat, moves so that the body portion 140 shakes, the influence to the probe portion 110 may be minimized by means of the flexible portion 120, and so it is possible to prevent the brain to be additionally damaged due to the shaking of the probe portion 110.

The flexible portion 120 is made of a relatively more flexible material in comparison to the material of the probe portion 110 and may be made of, for example, polyimide, parylene, polydimethylsiloxane, benzocyclobutene or the like.

The soluble portion 130 is coated on at least one surface of the flexible portion 120 and is made of a material dissolved by a solution in the cranium. The soluble portion 130 may be also coated on a partial region where the flexible portion 120 and the probe portion 110 are connected. However, since the soluble portion 130 is not coated on the entire probe portion 110, the entire thickness of the probe portion 110 does not increase. Moreover, the case where the soluble portion 130 is not dissolved to disturb the signal detection of the electrode 112 will not happen.

Since the soluble portion 130 is in a solid state before being dissolved by the solution in the cranium, when the probe portion 110 is inserted into the brain, the soluble portion maintains the insertion intensity. The soluble portion 130 is in a solid state at a room temperature and may be made of any material which can be dissolved by the solution in the cranium, for example sucrose, silk or the like.

The probe portion 110 is inserted into the brain through an opening formed in a part of the cranium. The cranium is spaced apart from the brain by a predetermined interval and a solution fills the gap. The soluble portion 130 is dissolved by the solution in the cranium to expose the flexible portion 120. If the flexible portion 120 is exposed, the flexible portion 120 may be bent as shown in FIG. 2, and even though the body portion 140 moves, it is possible to minimize the transfer of the shaking caused by the movement to the probe portion 110.

The body portion 140 is connected to the other end of the flexible portion 120, and may include an electronic device such as a PCB which processes a recording signal transmitted through the electrode 112 and the signal line 114.

Figure 3:
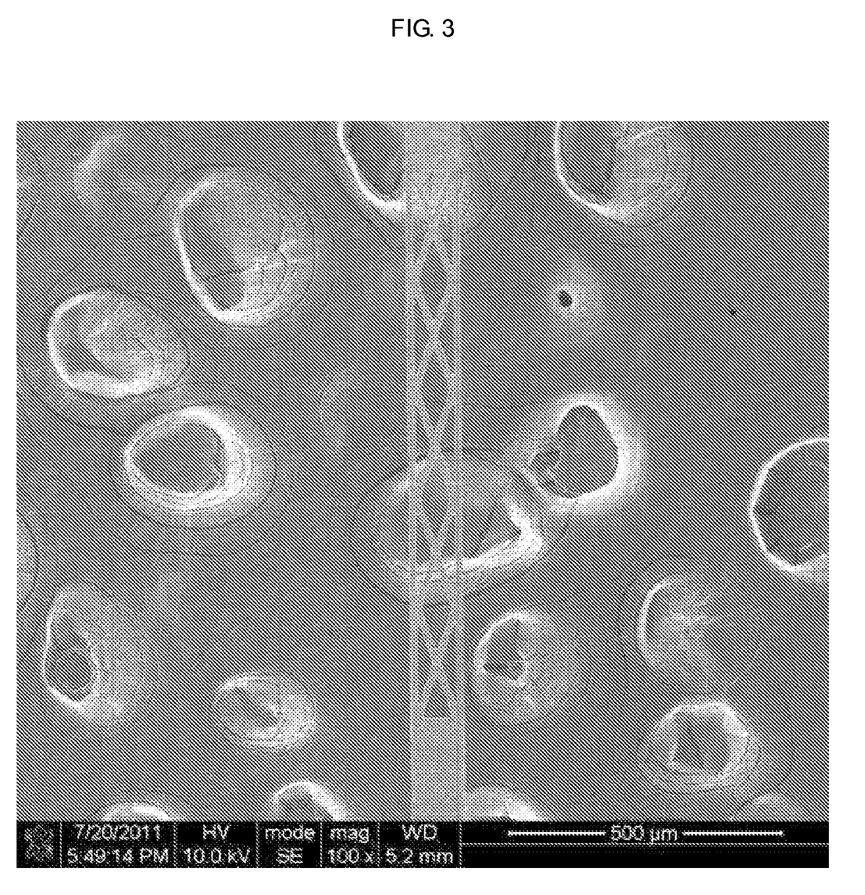
FIG. 3 is an SEM photograph showing the flexible portion of the micro probe of FIG. 1.

FIG. 3 is an SEM photograph showing the flexible portion of the micro probe of FIG. 1.

Referring to FIG. 3, the flexible portion 120 is formed with a lattice pattern. In case where the flexible portion 120 is configured in such a shape, it is possible not only to ensure the flexibility of the flexible portion 120 but also to reduce thickness.

Figure 4:
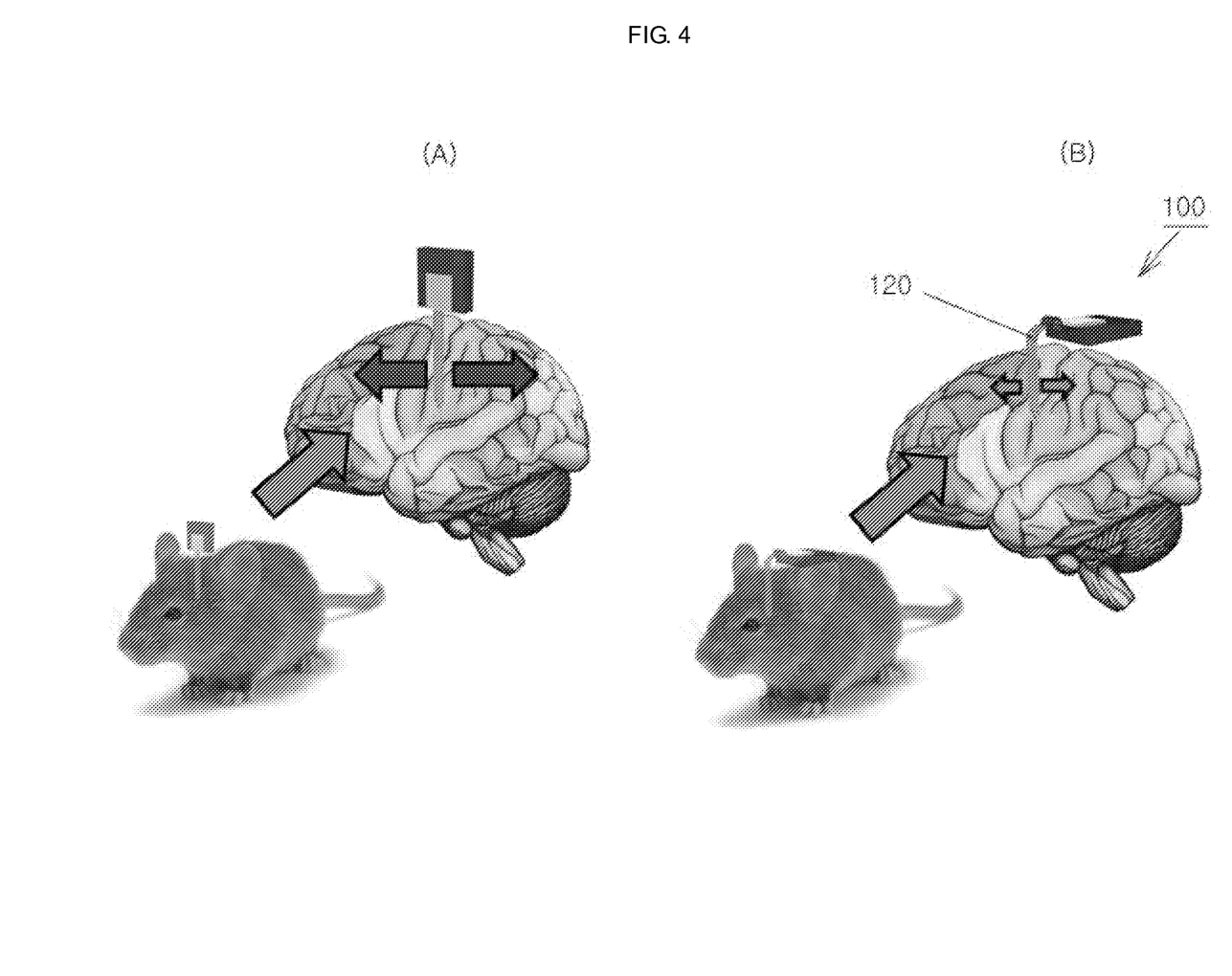
FIG. 4 is a diagram for comparing use states of a conventional micro probe and the micro probe according to the present disclosure.

FIG. 4 is a diagram for comparing use states of a conventional micro probe and the micro probe of the present disclosure.

Portion (A) of FIG. 4 shows a conventional micro probe. Since the conventional micro probe is entirely made of a rigid material, if shaking occurs at the outside of the micro probe after the conventional micro probe is inserted into the brain of an experimental subject, the vibration is transferred to the probe portion inserted into the brain, and so the probe portion shakes laterally, thereby causing a great brain damage.

However, in the micro probe of the present disclosure, as shown in Portion (B) of FIG. 4, if the probe portion 110 is inserted into the brain, the soluble portion 130 is dissolved to expose the flexible portion 120, and so, even though the body portion 140 disposed at an outside shakes, the influence to the probe portion 110 may be minimized by means of the flexible portion 120. Therefore, it is possible to prevent the brain from being additionally damaged due to the shaking of the probe portion 110.

FIGS. 5a to 5g are diagrams for illustrating a manufacturing method of a micro probe according to an embodiment of the present disclosure.

Figure 5A:
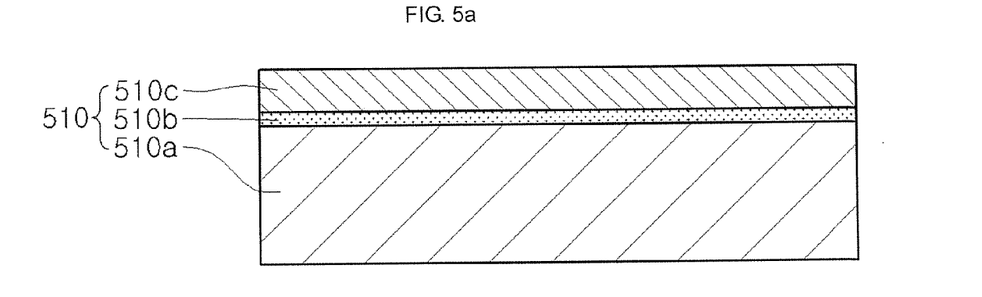
FIGS. 5a to 5g are diagrams for illustrating a manufacturing method of a micro probe according to an embodiment of the present disclosure.
Figure 5B:
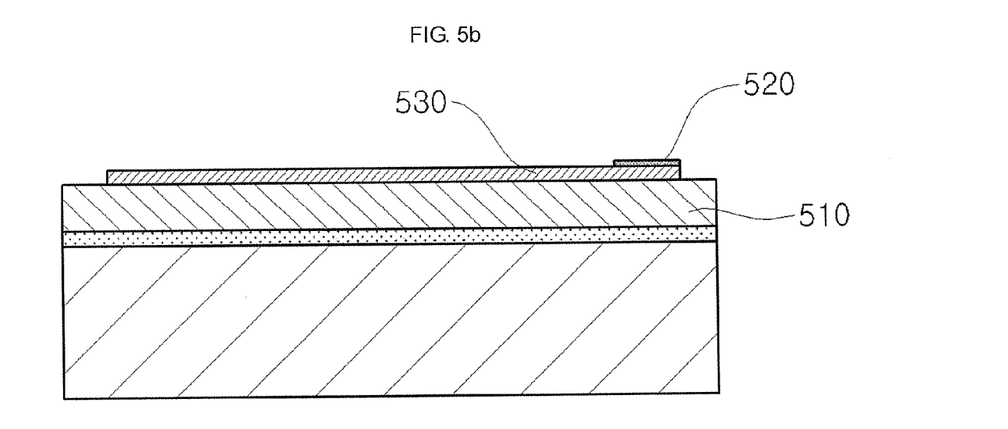

Referring to FIGS. 5a and 5b, a pattern of an electrode 520 and a signal line 530 are firstly formed on a wafer 510. The wafer 510 may be a silicon-on-insulator (SOI) wafer composed of a lower silicon 510a, an insulation substrate 510b and an upper silicon 510c.

Figure 5C:
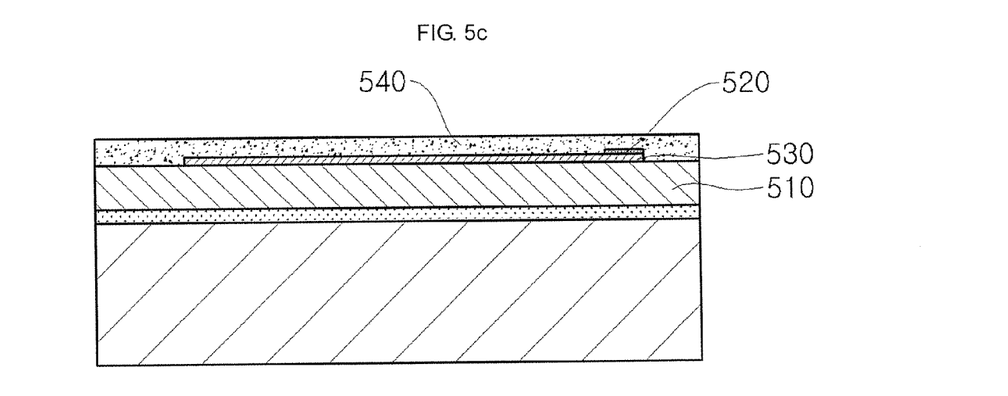
Figure 5D:
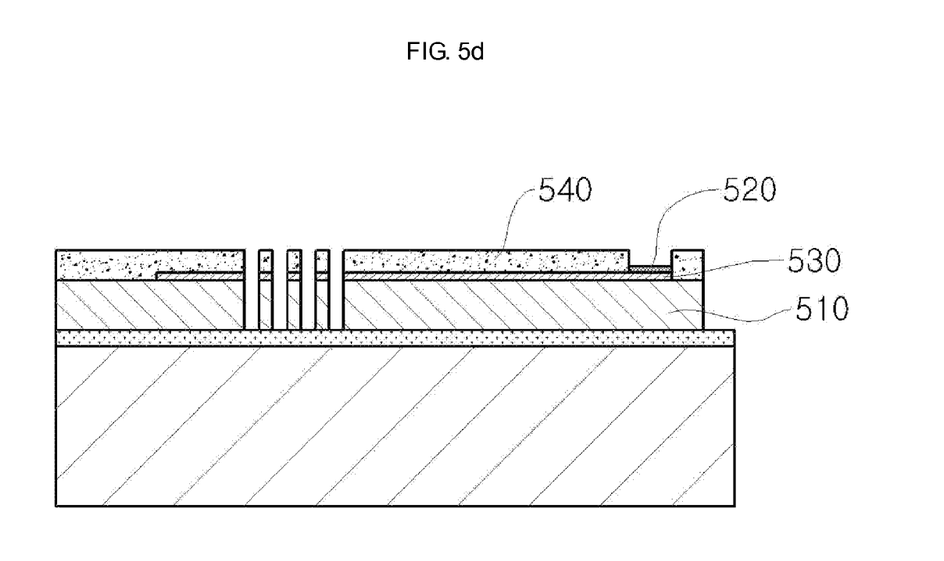

Next, as shown in FIG. 5c, a passivation layer 540 is deposited to cover the electrode 520 and the signal line 530.

Figure 6:
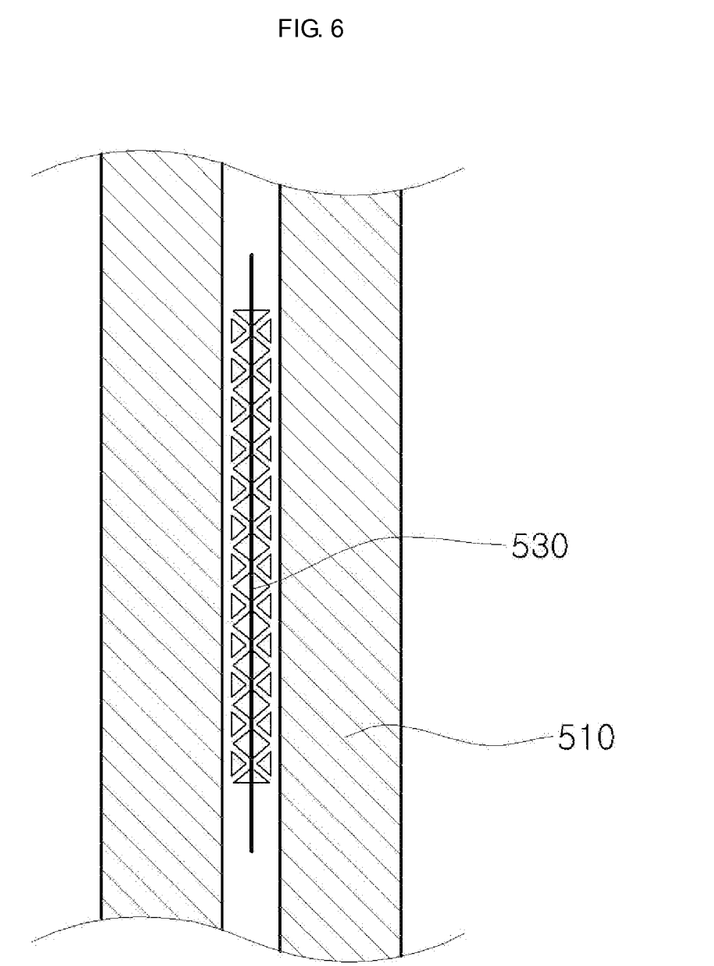
FIG. 6 is a plane view showing a part of an intermediate product of FIG. 5d, which is observed from the above.

Subsequently, a partial region of the wafer 510 where the signal line 530 passes is etched by means of an etching process. The signal line 530 is not etched by the etching process, and when the wafer 510 is etched, as shown in FIG. 6, the partial region of the wafer 510 may be etched into a lattice pattern. In addition, the passivation layer 540 deposited on the electrode 520 is etched by the etching process so that the electrode 520 may be exposed out.

Figure 5E:
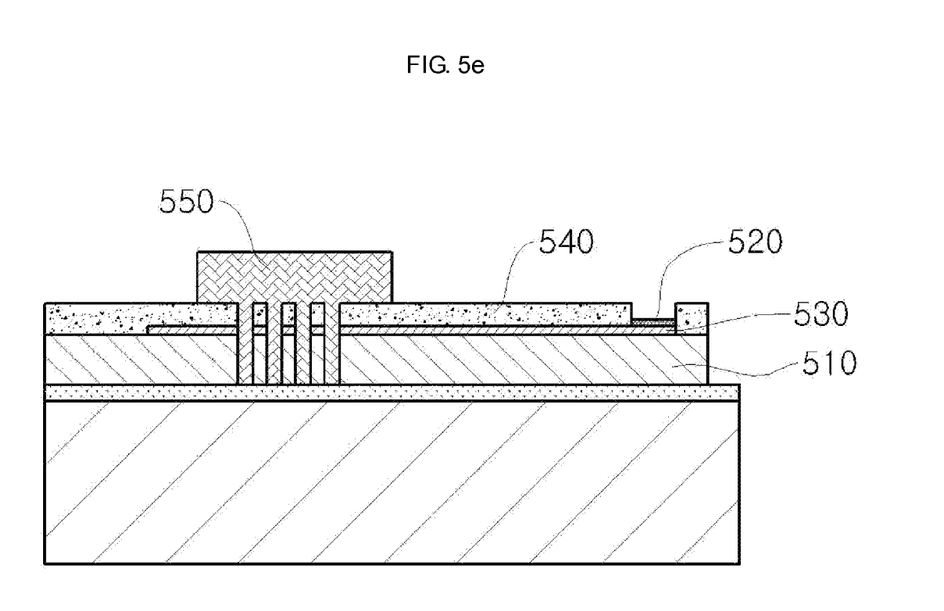

In succession, as shown in FIG. 5e, the flexible portion 550 is deposited while permeating the etched region of the wafer 510, and the completed shape of the flexible portion 550 may be implemented as shown in the SEM photograph of FIG. 3. As described above, the flexible portion 550 may be made of polyimide, parylene, polydimethylsiloxane or benzocyclobutene.

Figure 5F:
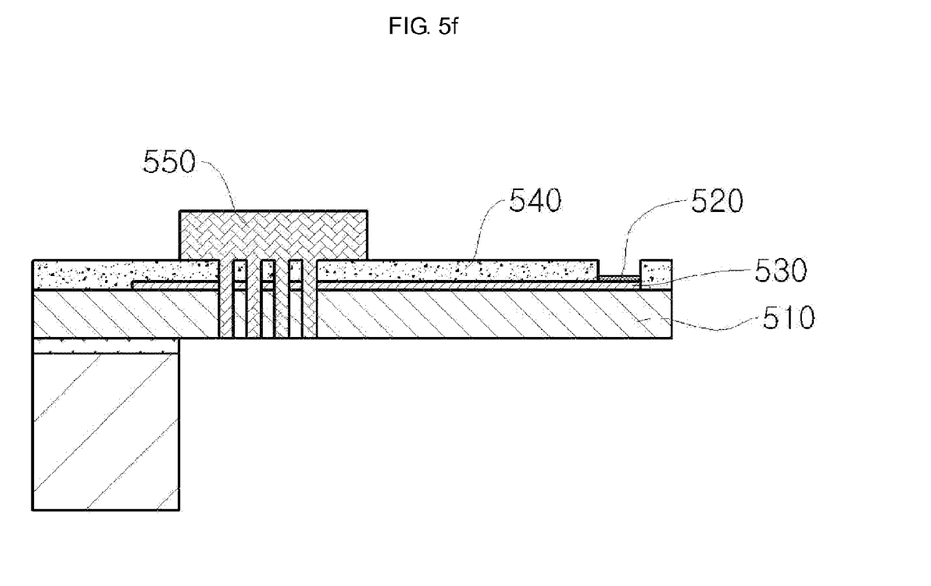

Subsequently, as shown in FIG. 5f, a region including a lower region of the flexible portion 550 is removed from the wafer 510 by means of a releasing process. This operation is performed to remove a partial region of the wafer 510 in order to form the probe portion and the flexible portion of the completed micro probe so that the thickness of the probe portion inserted into the brain of an experimental rat is reduced.

Figure 5G:
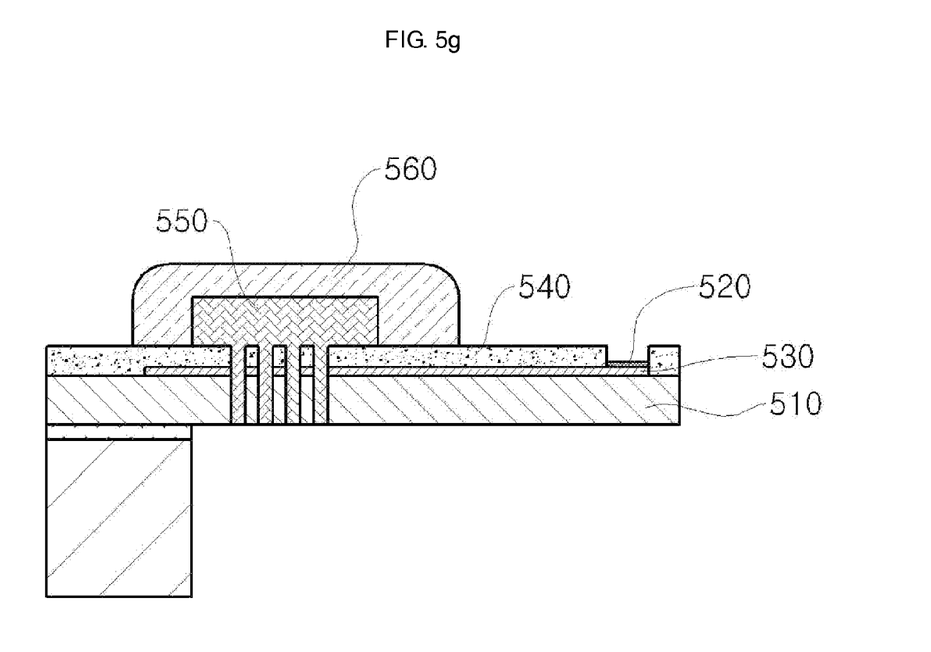

Next, as shown in FIG. 5g, at least one surface of the flexible portion 550 is coated with the soluble portion 560. The soluble portion 560 may be made of, for example, sucrose or silk, and the coated soluble portion 560 is kept in a solid state at a room temperature.

While the exemplary embodiments have been shown and described, it will be understood by those skilled in the art that various changes in form and details may be made thereto without departing from the spirit and scope of the present disclosure as defined by the appended claims.

What is claimed is:

1. A micro probe, comprising:
a probe portion made of a rigid material and serving as a portion inserted into a brain;
a flexible portion connected with a distal end of the probe portion and made of a flexible material;
a soluble portion coated on at least one surface of the flexible portion and made of a material which is dissolved by a solution in a cranium; and
a body portion connected with an end of the flexible portion other than an end connected with the probe portion,
wherein, after the probe portion is inserted into the brain through an opening formed in a part of the cranium, the soluble portion is dissolved in the cranium to expose the flexible portion,
wherein the body portion is disposed and used outside the cranium, and
wherein the flexible portion is formed with a lattice pattern.

2. The micro probe according to claim 1, wherein an electrode is disposed at a proximal end of the probe portion, and a signal line connected to the electrode extends to the body portion through the probe portion and the flexible portion.

3. The micro probe according to claim 1, wherein the flexible portion is made of polyimide, parylene, polydimethylsiloxane or benzocyclobutene.

4. The micro probe according to claim 1, wherein the soluble portion is made of sucrose or silk.

* * * * *